United States Patent [19]

Kirst et al.

[11] Patent Number: 4,468,511

[45] Date of Patent: Aug. 28, 1984

[54] C-20- AND C-23-MODIFIED MACROLIDE DERIVATIVES

[75] Inventors: Herbert A. Kirst, Indianapolis; John E. Toth, West Lafayette, both of Ind.

[73] Assignee: Eli Lilly and Company, Indianapolis, Ind.

[21] Appl. No.: 470,890

[22] Filed: Feb. 28, 1983

[51] Int. Cl.$^3$ ............................................. C07H 17/08
[52] U.S. Cl. ...................................... 536/7.1; 424/180
[58] Field of Search ......................................... 536/7.1

[56] References Cited

U.S. PATENT DOCUMENTS

| | | | |
|---|---|---|---|
| 3,459,853 | 8/1969 | Gorman et al. | 424/121 |
| 4,196,280 | 4/1980 | Umezawa et al. | 536/17 R |
| 4,279,896 | 7/1981 | Ganguly et al. | 424/180 |
| 4,304,856 | 12/1981 | Baltz et al. | 435/76 |
| 4,321,361 | 3/1982 | Baltz et al. | 536/17 R |
| 4,321,362 | 3/1982 | Baltz et al. | 536/17 R |
| 4,345,069 | 8/1982 | Sakakibara et al. | 536/7.1 |

FOREIGN PATENT DOCUMENTS

| | | |
|---|---|---|
| 33433 | 8/1981 | European Pat. Off. . |
| 56-122397 | 9/1981 | Japan . |
| 2081711 | 2/1982 | United Kingdom . |

OTHER PUBLICATIONS

H. Matsubara et al., "Chemical Transformation of Tylosin, a 16-Membered Macrolide, and its Structure-Activity Relationship", Chem. Pharm. Bull., 30 (1), 97–110 (1982).

S. Omura et al., "Novel Dimeric Derivatives of Leucomycins and Tylosin, Sixteen-Membered Macrolides", J. Med. Chem. 25, 271–275 (1982).

Derwent Abstract No. 71396Y of Japanese Unexamined Patent 2100-485 (Takeda), Aug. 23, 1977.

A. Tanaka et al., "Syntheses of 4'-Deoxy-Demycarosyl Tylosin and its Analogues", J. Antibiotics 34 (10), 1381–1384 (1981).

S. Satoi et al., "Mycinamicins, New Macrolide Antibiotics, I: Taxonomy, Production, Isolation, Characterization and Properties", J. Antibiotics 33 (4), 364–377 (1980).

A. Tanaka et al., "Syntheses of 23-Dialkylamino Derivatives of Mycaminosyl Tylonolide and 4'-Deoxymycaminosyl Tylonolide Effective Against Gram-Negative Bacteria", J. Antibiotics 35 (1), 113–116 (1982).

A. Tanaka et al., "Synthesis of 4'-Deoxymycaminosyl Tylonolide", J. Antibiotics 34 (10), 1374–1376 (1981).

A. Tanaka et al., "Synthesis of Derivatives of 4'-Deoxymycaminosyl Tylonolide and Mycaminosyl Tylonolide Modified at C-23", J. Antibiotics 34 (10), 1377–1380 (1981).

Derwent Abstract No. 92092A/51 of Japanese Unexamined Patent 3130-686 (Toyo Brewing), Nov. 14, 1978.

Derwent Abstract No. 008688/01 of Japanese Unexamined Patent 3132-584 (Toyo Brewing), Nov. 18, 1978.

Derwent Abstract No. 65537B/36 of Japanese Unexamined Patent 4095-584 (Toyo Brewing), Jul. 28, 1979.

Primary Examiner—Johnnie R. Brown
Attorney, Agent, or Firm—Nancy J. Harrison; Arthur R. Whale

[57] ABSTRACT

C-20- and C-23-Modified macrolide derivatives of demycinosyltylocin (DMT), 5-O-mycaminosyltylonolide (OMT) 23-de(mycinosyloxy)tylosin, 23-deoxy-OMT, 20-dihydro-20-deoxy-DMT and 20-dihydro-20-deoxy-OMT are useful antibiotics or intermediates to antibiotics.

31 Claims, No Drawings

C-20- AND C-23-MODIFIED MACROLIDE DERIVATIVES

SUMMARY OF THE INVENTION

This invention relates to C-20- and C-23-modified macrolide derivatives having formula 1:

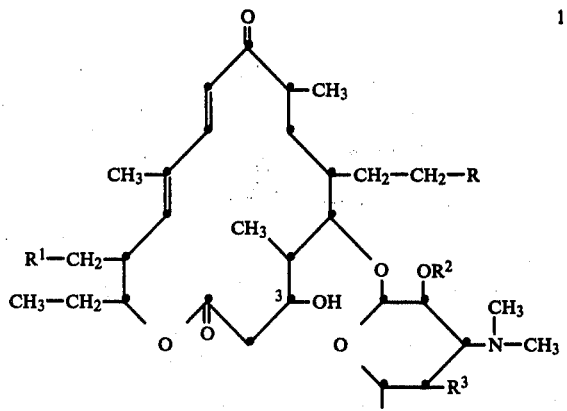

wherein
R is hydrogen, iodo, bromo, chloro, fluoro, cyano, —OR⁴, —OAr, —SR⁵, azido, —NR⁶R⁷, or N-phthalimido;

R¹ is
(i) hydrogen or —OH;
(ii) chloro, fluoro, —OAr, -O-tetrahydrofuranyl, -O-tetrahydropyranyl, —SR⁵, azido, —NR⁶R⁷, or N-phthalimido;
(iii) a monocyclic amino group of the formula —N(CH₂)ₙ which is optionally substituted at one or more of the carbon atoms by a C₁-C₃-alkyl, hydroxyl, methoxyl, ethoxyl, —N(R⁸)₂,

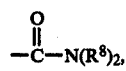

carbomethoxy, carboethoxy, or phenyl group; and n is an integer from 4 through 15;
(iv) a monocyclic saturated or unsaturated nitrogen-containing heterocyclic ring bonded through the nitrogen atom, said ring having (1) from 5 to 7 ring atoms which include up to 3 additional heteroatoms selected from nitrogen, oxygen and sulfur, and (2) up to 3 substituent groups selected from methyl, ethyl and phenyl; or
(v) a bicyclic or tricyclic secondary amino group selected from 1,2,3,4-tetrahydroquinolin-1-yl; decahydroquinolin-1-yl; 1,2,3,4-tetrahydroisoquinolin-2-yl; decahydroisoquinolin-2-yl; indolin-1-yl; isoindolin-2-yl; decahydrocyclohepta[b]pyrrol-1-yl; decahydrocyclohepta[c]pyrrol-2-yl; decahydrocyclopent[c]azepin-2-yl; decahydrocyclopent[d]azepin-3-yl; 2,3,4,5-tetrahydro-1H-2-benzazepin-2-yl; 2,3,4,5-tetrahydro-1H-3-benzazepin-3-yl; azabicycloheptanyl; azabicyclooctanyl; azabicyclononanyl; azabicyclodecanyl or azatricyclodecanyl;

R² is hydrogen, optionally substituted C₁-C₅-alkanoyl or optionally substituted benzoyl, phenylacetyl or phenylpropionyl;
R³ is hydrogen, hydroxyl, optionally substituted C₁-C₅-alkanoyloxy or optionally substituted benzoyloxy, phenylacetoxy or phenylpropionyloxy or

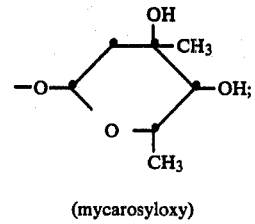

(mycarosyloxy)

R⁴ is hydrogen, optionally substituted C₁-C₄-alkyl, cyclohexyl, optionally substituted benzyl, phenethyl or phenoxyethyl;
Ar is
(i) phenyl, derivatized phenyl, or naphthyl;
(ii) an optionally substituted heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl, benzotriazolyl, benzoxazolyl, benzimidazolyl, carbazolyl, or acridinyl; or
(iii) optionally substituted C₁-C₅-alkanoyl; optionally substituted benzoyl, phenylacetyl, phenylpropionyl, phenoxyacetyl or phenylthioacetyl; methanesulfonyl; trifluoromethanesulfonyl; or optionally substituted phenylsulfonyl;
R⁵ is optionally substituted C₁-C₄-alkyl; cyclohexyl; optionally substituted phenyl, benzyl or phenethyl; or an optionally substituted heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl;
R⁶ is hydrogen, optionally substituted C₁-C₆-alkyl, phenyl, benzyl, phenethyl or C₃-C₈-cycloalkyl;
R⁷ is an R⁶ group or optionally substituted C₁-C₅-alkanoyl, optionally substituted benzoyl, phenylacetyl, phenylpropionyl, phenoxyacetyl or phenylthioacetyl, or alkoxycarbonyl; and
R⁸ is hydrogen, methyl, ethyl, n-propyl or isopropyl or the R⁸ groups taken together form a polymethylene moiety such that —N(R⁸)₂ constitutes a cyclic amino group selected from pyrrolidinyl, piperidinyl, hexahydroazepinyl or octahydroazocinyl; provided (1) that, when R or R⁴ is hydrogen, R¹ cannot be hydrogen or —OH; (2) that, when R or R¹ is —NHR⁶ or R⁸ is hydrogen, R² must be hydrogen, R³ must be hydrogen, hydroxyl, or mycarosyloxy and Ar cannot be a type (iii) substituent; and (3) that, when R² is hydrogen, R³ must be hydrogen, hydroxyl or mycarosyloxy; and to the salts, particularly the acid addition salts, of these compounds. The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to a group of C-20- and C-23-modified macrolide derivatives and to their salts, particularly the acid addition salts. This invention also relates to methods of treating certain infections with, methods of promoting growth in animals with, and pharmaceutical compositions comprising the specified derivatives and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

The derivatives of this invention are compounds of formula 1:

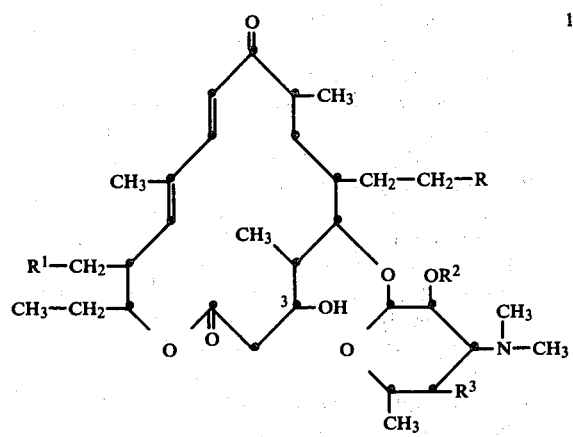

wherein

R is hydrogen, iodo, bromo, chloro, fluoro, cyano, —$OR^4$, —OAr, —$SR^5$, azido, —$NR^6R^7$, or N-phthalimido;

$R^1$ is
  (i) hydrogen or —OH;
  (ii) chloro, fluoro, —OAr, -O-tetrahydrofuranyl, -O-tetrahydropyranyl, —$SR^5$, azido, —$NR^6R^7$, or N-phthalimido;
  (iii) a monocyclic amino group of the formula —$N(CH_2)_n$ which is optionally substituted at one or more of the carbon atoms by a $C_1$–$C_3$-alkyl, hydroxyl, methoxyl, ethoxyl, —$N(R^8)_2$,

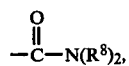

carbomethoxy, carboethoxy, or phenyl group; and n is an integer from 4 through 15;
  (iv) a monocyclic saturated or unsaturated nitrogen-containing heterocyclic ring bonded through the nitrogen atom, said ring having (1) from 5 to 7 ring atoms which include up to 3 additional heteroatoms selected from nitrogen, oxygen and sulfur, and (2) up to 3 substituent groups selected from methyl, ethyl and phenyl; or
  (v) a bicyclic or tricyclic secondary amino group selected from 1,2,3,4-tetrahydroquinolin-1-yl; decahydroquinolin-1-yl; 1,2,3,4-tetrahydroisoquinolin-2-yl; decahydroisoquinolin-2-yl; indolin-1-yl; isoindolin-2-yl; decahydrocyclohepta[b]pyrrol-1-yl; decahydrocyclohepta[c]pyrrol-2-yl; decahydrocyclopent[c]azepin-2-yl; decahydrocyclopent[d]azepin-3-yl; 2,3,4,5-tetrahydro-1H-2-benzazepin-2-yl; 2,3,4,5-tetrahydro-1H-3-benzazepin-3-yl; azabicycloheptanyl; azabicyclooctanyl; azabicyclononanyl; azabicyclodecanyl or azatricyclodecanyl;

$R^2$ is hydrogen, optionally substituted $C_1$–$C_5$-alkanoyl or optionally substituted benzoyl, phenylacetyl or phenylpropionyl;

$R^3$ is hydrogen, hydroxyl, optionally substituted $C_1$–$C_5$-alkanoyloxy or optionally substituted benzoyloxy, phenylacetoxy or phenylpropionyloxy or

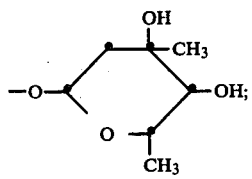

(mycarosyloxy)

$R^4$ is hydrogen, optionally substituted $C_1$–$C_4$-alkyl, cyclohexyl, optionally substituted benzyl, phenethyl or phenoxyethyl;

Ar is
  (i) phenyl, derivatized phenyl, or naphthyl;
  (ii) an optionally substituted heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl, benzotriazolyl, benzoxazolyl, benzimidazolyl, carbazolyl, or acridinyl; or
  (iii) optionally substituted $C_1$–$C_5$-alkanoyl; optionally substituted benzoyl, phenylacetyl, phenylpropionyl, phenoxyacetyl or phenylthioacetyl; methanesulfonyl; trifluoromethanesulfonyl; or optionally substituted phenylsulfonyl;

$R^5$ is optionally substituted $C_1$–$C_4$-alkyl; cyclohexyl; optionally substituted phenyl, benzyl or phenethyl; or an optionally substituted heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl;

$R^6$ is hydrogen, optionally substituted $C_1$–$C_6$-alkyl, phenyl, benzyl, phenethyl or $C_3$–$C_8$-cycloalkyl;

$R^7$ is an $R^6$ group or optionally substituted $C_1$–$C_5$-alkanoyl, optionally substituted benzoyl, phenylacetyl, phenylpropionyl, phenoxyacetyl or phenylthioacetyl, or alkoxycarbonyl; and $R^8$ is hydrogen, methyl, ethyl, n-propyl or isopropyl or the $R^8$ groups taken together form a polymethylene moiety such that —$N(R^8)_2$ constitutes a cyclic amino group selected from pyrrolidinyl, piperidinyl, hexahydroazepinyl or octahydroazocinyl; provided (1) that, when R or $R^4$ is hydrogen, $R^1$ cannot be hydrogen or —OH; (2) that, when R or $R^1$ is —$NHR^6$ or $R^8$ is hydrogen, $R^2$ must be hydrogen, $R^3$ must be hydrogen, hydroxyl, or mycarosyloxy and Ar cannot be a type (iii) substitutent; and (3) that, when $R^2$ is hydrogen, $R^3$ must be hydrogen, hydroxyl or mycarosyloxy; and to the salts, particularly the acid addition salts, of these compounds.

Monocyclic saturated or unsaturated nitrogen-containing heterocyclic rings which are bonded through the nitrogen atom and which have from five to seven ring atoms, including up to three additional heteroatoms selected from nitrogen, oxygen and sulfur, include groups such as pyrrolyl, pyrazolyl, imidazolyl, 1,2,4-oxadiazinyl, 1,3,4-thiadiazinyl, 1,2,4-triazolyl, 1H-tetrazolyl, 1,4-diazepinyl, morpholino, thiomorpholino, piperazinyl, thiazolidinyl, oxazolidinyl, and tetrahydro-1,4-thiazin-4-yl. Such rings can have up to three substituents selected from methyl, ethyl and phenyl on appropriate carbon and/or nitrogen ring atoms(s).

The term "$C_1$–$C_5$-alkanoyl" as used herein means an acyl moiety derived from a carboxylic acid containing from one to five carbon atoms. In such a moiety, the alkyl group can be straight, branched, or cyclic. When optionally substituted, the alkyl group can bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups. The term "$C_1$–$C_5$-alkanoyloxy" refers to the corresponding acyloxy moiety.

The terms "optionally substituted benzoyl, phenylacetyl, phenylpropionyl, phenoxyacetyl or phenylthioacetyl", "optionally substituted benzoyl, phenylacetyl or phenylpropionyl", "optionally substituted benzoyloxy, phenylacetoxy or phenylpropionyloxy", "optionally substituted phenyl, benzyl or phenethyl", "optionally substituted benzyl, phenethyl or phenoxyethyl" and "optionally substituted phenylsulfonyl" mean that the phenyl portion of the moiety is optionally substituted by from one to five halo or methyl groups or by from one to two methoxyl, nitro or hydroxyl groups.

The term "derivatized phenyl" refers to a phenyl group which has from one to five halo, methoxyl or $C_1$–$C_4$-alkyl substituents, or from one to two nitro, amino, methylamino, ethylamino, dimethylamino, diethylamino, $C_4$–$C_{10}$-methyleneamino, azido, hydroxy, hydroxymethyl, aminomethyl, (methylamino)methyl, (ethylamino)methyl, (dimethylamino)methyl, (diethylamino)methyl, ($C_4$–$C_{10}$-methyleneamino)methyl, formyl, acetyl, benzoyl, methoxycarbonyl, ethoxycarbonyl, carboxamido, N-methylcarboxamido, N,N-dimethylcarboxamido, cyano, phenyl, phenoxy or benzyl substituents.

The term "optionally substituted heteroaryl group" as used herein means that the heteroaryl group may have at least one suitable substituent(s) such as a $C_1$–$C_4$-alkyl, halo, methoxy, ethoxy, hydroxy (or the keto tautomer) or phenyl group.

The terms "$C_1$–$C_3$-alkyl", "$C_1$–$C_4$-alkyl" or "$C_1$–$C_6$-alkyl" as used herein mean a straight- or branched-chain alkyl group containing the specified number of carbon atoms. Such groups include methyl, ethyl, isopropyl, n-butyl, tert-butyl, n-hexyl, and the like. "Optionally substituted" $C_1$–$C_4$-alkyl or $C_1$–$C_6$-alkyl means that the alkyl group contains one or more fluoro or chloro substituents.

"$C_3$–$C_8$-cycloalkyl" refers to a cycloalkyl group containing from three to eight carbon atoms. Examples of such groups are cyclopropyl, cyclohexyl and cyclooctyl.

The term "alkoxycarbonyl" represents a member of a group selected from t-butoxycarbonyl, methoxycarbonyl, ethoxycarbonyl, 2,2,2-trichloroethoxycarbonyl, phenoxycarbonyl and benzyloxycarbonyl.

The term "$C_4$–$C_{10}$-methyleneamino" represents a cyclic amino substituent of the formula —$N(CH_2)_n$ wherein n is an integer from four to ten. Pyrrolidinyl, piperidinyl, and octahydroazocinyl are examples of such groups.

The modified macrolide derivatives of this invention are prepared from the group of macrolide antibiotics which includes demycinosyltylosin (DMT), 20-dihydro-23-demycinosyltylosin (dihydro-DMT), 23-de(mycinosyloxy)tylosin (DMOT), 20-dihydro-23-de(mycinosyloxy)tylosin (dihydro-DMOT), 5-O-mycaminosyltylonolide (OMT), 20-dihydro-5-O-mycaminosyltylonolide (dihydro-OMT), 23-deoxy-5-O-mycaminosyltylonolide (DOMT), 20-dihydro-23-deoxy-5-O-mycaminosyltylonolide (dihydro-DOMT), 20-dihydro-20-deoxy-23-demycinosyltylosin (DH-DO-DMT) and 20-dihydro-20-deoxy-5-O-mycaminosyltylonolide (DH-DO-OMT).

DMT, dihydro-DMT, DMOT, dihydro-DMOT, DOMT, and dihydro-DOMT are antibiotics described by Richard H. Baltz, Gene M. Wild, and Eugene T. Seno in U.S. Pat. Nos. 4,321,361 and 4,321,362, both of which issued on Mar. 23, 1982. DH-DO-DMT and DH-DO-OMT are described by Richard H. Baltz, Herbert A. Kirst, Gene H. Wild and Eugene T. Seno in U.S. Pat. No. 4,304,856, which issued Dec. 8, 1981. OMT and dihydro-OMT are described by Marvin Gorman and Robert D. Morin in U.S. Pat. No. 3,459,853, issued on Aug. 5, 1969.

The structures of the starting antibiotics are shown in formulas 2–11:

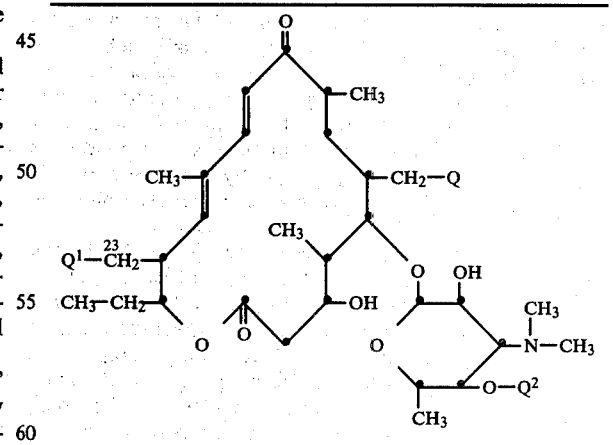

| | Q | $Q^1$ | $Q^2$ |
|---|---|---|---|
| 2 DMT: | —CHO | —OH | mycarosyl |
| 3 dihydro-DMT: | —CH$_2$OH | —OH | " |
| 4 OMT: | —CHO | —OH | H |
| 5 dihydro-OMT: | —CH$_2$OH | —OH | H |
| 6 DMOT: | —CHO | H | mycarosyl |
| 7 dihydro-DMOT: | —CH$_2$OH | H | " |
| 8 DOMT: | —CHO | H | H |
| 9 dihydro-DOMT: | —CH$_2$OH | H | H |

-continued

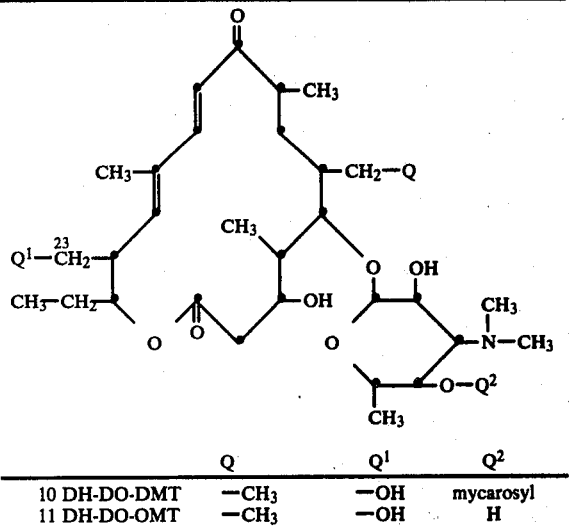

|    | Q | Q¹ | Q² |
|----|---|----|----|
| 10 DH-DO-DMT | —CH₃ | —OH | mycarosyl |
| 11 DH-DO-OMT | —CH₃ | —OH | H |

Preparation of many of the C-20-modified derivatives of this invention involves first reducing the C-20 aldehyde group of DMT, OMT, DMOT or DOMT to give the corresponding 20-dihydro compounds of formulas 3, 5, 7 and 9. The C-20 hydroxyl group of these compounds may then be replaced by the desired substituent. Replacement can be accomplished by a variety of synthetic methodology. For example, one particularly useful method exemplified in this application is the diethylazodicarboxylate/triphenylphosphine (DEAD) reaction [see O. Mitsunobu, *Synthesis* 1(1), 1–28 (1981)].

The compounds of formula 1 wherein R is chloro, bromo or iodo may be conveniently prepared by methods known in the art from the appropriate 20-dihydro compound using triphenylphosphine and a halogen source such as carbon tetrachloride, carbon tetrabromide, carbon tetraiodide or iodine.

20-O-Carboxylate and sulfonate derivatives, e.g., compounds of formula 1 wherein R⁴ is an acyl or sulfonyl moiety, may be prepared by acylation procedures well known in the art.

Compounds of formula 1 wherein R⁴ is methanesulfonyl, trifluoromethanesulfonyl or optionally substituted phenylsulfonyl, as well as compounds wherein R is iodo or bromo, are useful as intermediates for the preparation of additional compounds of this invention via $S_N1$ or $S_N2$ substitution reactions. Suitable reaction conditions for displacing a leaving group by a nucleophile via either an $S_N1$ or $S_N2$ mechanism are well exemplified in the art of nucleophilic substitution reactions.

The formula 1 compounds wherein R is —NHR⁷ and R⁷ is an acyl group are prepared via the 20-azido derivative (R=N₃). The 20-azido derivative is first reduced to the 20-amino derivative (R=NH₂); triphenylphosphine in aqueous tetrahydrofuran (THF) is an example of a suitable reducing agent for this purpose. The 20-amino derivative can then be selectively acylated on the amino group, using standard acylation procedures, to give those derivatives wherein R₇ is an acyl group.

It should be noted that, when the compounds of formulas 3 or 5 are used as starting materials, two primary hydroxyl groups are present which react in a similar manner. The primary hydroxyl group at C-20, however, is usually replaced more rapidly than the hydroxyl group at C-23. Although many of the procedures described supra give mixtures of 20-monosubstituted derivatives and 20,23-disubstituted derivatives, such mixtures can be readily separated by techniques known in the art, such as, for example, chromatography using silica gel as the adsorbent. Formation of C-20-monosubstituted derivatives may be optimized by not carrying the reaction to completion, for example, by using less than two molar equivalents of reactant(s). Conversely, when C-20, C-23-disubstituted derivatives are sought, the reaction should be carried to completion and two molar equivalents or an excess of reactant(s) should be used.

Compounds wherein the substituent R¹ differs from the substituent R may also be prepared by modifying the hydroxyl group at C-23 before reducing the aldehyde at C-20. Procedures for modifying the C-23 position are provided in our copending applications Ser. Nos. 399,656 and 399,657, filed July 16, 1982, which are incorporated herein by reference. In addition, the DEAD reaction discussed supra may conveniently be used to prepare many of the C-23-modified compounds. This procedure for modification of primay hydroxyl groups is discussed further in our application Ser. No. 417,248, filed Sept. 13, 1982, now U.S. Pat. No. 4,443,436. Other procedures for modification of the C-23-position are described by A. Tanaka et al. in *J. Antibiotics* 35 (1) 113–116, (1982). Procedures for the preparation of 23-esters are discussed in Kirst's copending applications Ser. Nos. 330,341, now U.S. Pat. No. 4,401,660 and 330,294, now U.S. Pat. No. 4,396,613 and in our copending application Ser. No. 330,295, now abandoned, all of which were filed Dec. 14, 1981, and by Tanaka, et al., in *J. Antibiotics* 34 (10), 1377–1379 (1981).

When preparing formula 1 compounds wherein R is hydrogen, compounds 10 and 11 may be used as starting materials and modified at the C-23 hydroxyl group as previously described.

An alternate method for preparing compounds with different substituents at C-20 and C-23 is to modify the C-20 position of a macrolide not having a free C-23 hydroxyl group. One example of this approach is to prepare a C-20-modified derivative of desmycosin, tylosin, macrocin, lactenocin, demethylmacrocin and demethyllactenocin, as described in our application Ser. No. 417,248, filed Sept. 13, 1982, followed by hydrolysis of the neutral sugar(s), using procedures known in the art (see, for example, U.S. Pat. No. 3,459,853). By this procedure, a 20-modified derivative of OMT can be selectively prepared, which in turn can be modified at the C-23 position, as discussed supra.

Use of a protecting group for the hydroxyl group at C-23 of OMT and DMT prior to reduction of the aldehyde also permits selective modification of C-20. Removal of the protecting group after appropriate modification of C-20 yields C-20-modified derivatives having a hydroxyl group at C-23, which may then be modified as outlined previously. Examples of useful protecting groups are ester moieties, such as acetyl and trichloroacetyl, and groups such as tetrahydropyranyl and tetrahydrofuranyl. The C-23 ester derivatives may be prepared as described in the copending applications previously discussed (Ser. Nos. 330,341, 330,294 and 330,295). The tetrahydropyranyl and tetrahydrofuranyl protecting groups are described, for example, by Tanaka et al., supra.

The modified derivatives of OMT, DOMT and DH-DO-OMT can also be prepared by acidic hydrolysis of mycarose from the corresponding modified derivatives of DMT, DMOT and DH-DO-DMT, respectively, prepared by the methods previously described. Procedures for the acidic hydrolysis of mycarose from DMT and DMOT tto form OMT and DOMT, respectively, are found in U.S. Pat. Nos. 4,321,361 and 4,321,362. Acidic hydrolysis of DH-DO-DMT to give DH-DO-OMT is described in U.S. Pat. No. 4,304,856.

Additional formtula 1 derivatives wherein R is an —N(R$^6$)$_2$ group involve in a formal sense reductive amination of the C-20 aldehyde group of DMT, OMT, DMOT, and DOMT. This can be accomplished by two methods.

Method 1:

A derivative with a leaving group at C-20 (iodo, triflate, etc.), prepared as described supra, is reacted with the appropriate amine in a suitable solvent, such as acetonitrile, until the desired 20-modified derivative is formed via displacement of the C-20 leaving group by the nucleophilic amine.

Method 2:

In this method, the aldehyde group of compound 2, 4, 6, or 8 is reacted directly with the corresponding amine in the presence of a suitable reducing agent in an appropriate solvent until the desired product is formed. Sodium cyanoborohydride is an example of a suitable reducing agent, and anhydrous methanol is a useful solvent for this reaction. The reaction may be carried out under a nitrogen atmosphere, but this is usually not required. With less reactive amines, more forcing conditions for forming the intermediates iminium complex between the macrolide and amine may be required, e.g. heating, use of a drying agent or water scavenger or heating under conditions of azeotropic removal of water in solvents such as benzene or toluene.

The 4'-deoxy derivatives of this invention, i.e. the compounds of formula 1 wherein R$^3$ is hydrogen, are readily prepared by procedures analogous to those described supra, using 4'-deoxy-OMT, 4'-deoxy-DOMT or 4'-deoxy-DH-DO-OMT as the starting material. These starting materials can be prepared via procedures outlined in *J. Antibiotics* 34, 1381-1384 (1981). Alternatively, deoxygenation at 4' may be accomplished in OMT, DOMT or DH-DO-OMT subsequent to modification of the C-20 and/or C-23 positions.

The formula 1 compounds which are ester derivatives are prepared by esterifying the respective C-20 and/or C-23-modified derivative on the 2', 4', and/or 23-hydroxyl groups (when present) by treatment with acylating agents, using standard methods exemplified in the art. The preparation of 2'-O-ester derivatives of the C-20- and/or C-23-modified derivatives is accomplished by procedures similar to those described by Baltz et al. in U.S. Pat. Nos. 4,321,361 and 4,321,362. Esterification of the 2', 4' and/or 23-hydroxyl groups of these modified derivatives may be accomplished by acylation of the hydroxyl groups using similar procedures as outlined in the previously discussed applications Ser. Nos. 330,341, 330,295, and 330,294.

Alternatively, the formula 1 compounds which are esters may be prepared by starting with the appropriate esters of compounds 2-11, prepared as described supra. Furthermore, it should be noted that the formula 1 ester compounds can be hydrolyzed to yield the corresponding formula 1 compounds, thus utilizing the esters as protecting groups during reactions to modify the C-20 and/or C-23 positions.

The C-20-modified derivatives of this invention form salts, particularly acid addition salts. These acid addition salts are also useful as antibiotics and are a part of this invention. In another aspect, such salts are useful as intermediates, for example, for separating and purifying the derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention.

Illustrative formula 1 compounds of this invention are listed in Table I.

TABLE I

Illustrative Formula 1 Compounds

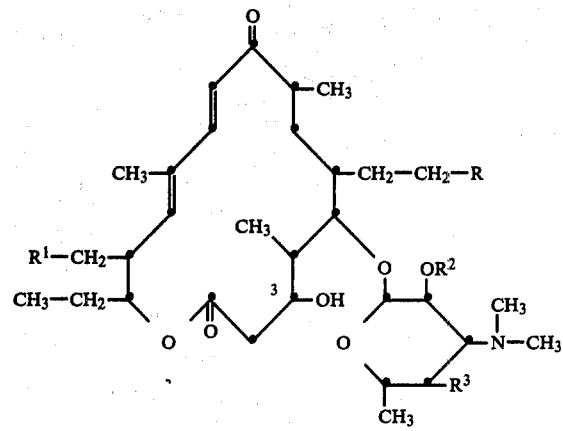

| Compound No. | R | R$^1$ | R$^2$ | R$^3$ |
|---|---|---|---|---|
| 1 | phenylacetoxy | OH | H | —OH |
| 2 | N,N—dimethylamino | " | " | " |

TABLE I-continued
Illustrative Formula 1 Compounds

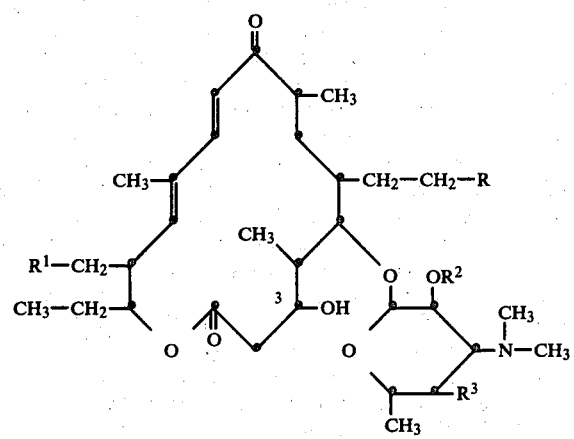

| Compound No. | R | R[1] | R[2] | R[3] |
|---|---|---|---|---|
| 3 | N—methylamino | " | " | " |
| 4 | N—benzylamino | " | " | " |
| 5 | N—(phenethyl)amino | " | " | " |
| 6 | N—phthalimido | " | " | " |
| 7 | phenoxy | " | " | " |
| 8 | p-(phenoxy)phenoxy | " | " | " |
| 9 | phenylthio | " | " | " |
| 10 | (1-methyltetrazol-5-yl)thio | " | " | " |
| 11 | azido | OH | H | —OH |
| 12 | amino | " | " | " |
| 13 | (N—phenylacetyl)amino | " | " | " |
| 14 | iodo | " | " | " |
| 15 | chloro | " | " | " |
| 16 | N—(phenethyl)amino | " | " | mycarosyloxy |
| 17 | N—phthalimido | " | " | " |
| 18 | phenoxy | " | " | " |
| 19 | azido | " | " | " |
| 20 | (1-methyltetrazol-5-yl)thio | " | " | " |
| 21 | N—(phenethyl)amino | H | H | —OH |
| 22 | N—phthalimido | " | " | " |
| 23 | phenoxy | " | " | " |
| 24 | azido | " | " | " |
| 25 | N—(benzyl)amino | " | " | mycarosyloxy |
| 26 | N—phthalimido | " | " | " |
| 27 | phenoxy | H | H | mycarosyloxy |
| 28 | azido | " | " | " |
| 29 | phenylthio | " | " | " |
| 30 | phenylacetoxy | phenylacetoxy | H | —OH |
| 31 | N—phthalimido | N—phthalimido | " | " |
| 32 | phenoxy | phenoxy | " | " |
| 33 | phenoxy | phenylpropionyloxy | " | " |
| 34 | phenoxy | octahydroazocin-1-yl | " | " |
| 35 | (N—phenylacetyl)amino | " | " | " |
| 36 | phenylthio | azabicyclononanyl | " | " |
| 37 | chloro | 4-phenylpiperidino | " | " |
| 38 | N—phthalimido | N—phthalimido | " | mycarosyloxy |
| 39 | phenoxy | hexahydroazepin-1-yl | " | " |
| 40 | H | acetoxy | acetyl | acetoxy |
| 41 | H | phenylacetoxy | H | —OH |
| 42 | H | phenylthio | " | " |
| 43 | H | octahydroazocin-1-yl | " | " |
| 44 | H | 3-(dimethylamino)-phenoxy | H | —OH |
| 45 | H | 4-hydroxypiperidino | " | " |
| 46 | H | (pyridin-3-yl)oxy | " | " |
| 47 | H | 2,3-(dimethoxy)phenoxy | " | " |
| 48 | H | phenoxy | " | " |
| 49 | H | 3-azabicyclononan-3-yl | " | " |
| 50 | H | 4-phenylpiperidino- | " | " |
| 51 | —OH | phenoxy | acetyl | acetoxy |
| 52 | —OH | phenylpropionyloxy | H | —OH |
| 53 | —OH | octahydroazocin-1-yl | H | H |
| 54 | phenylacetoxy | —OH | acetyl | acetoxy |
| 55 | phenylacetoxy | phenylacetoxy | acetyl | acetoxy |

TABLE I-continued

Illustrative Formula 1 Compounds

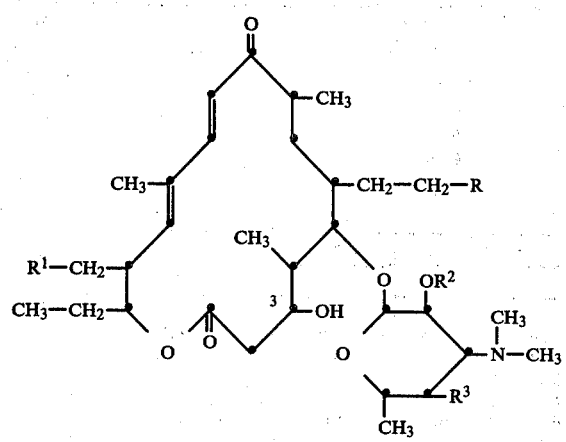

| Compound No. | R | R¹ | R² | R³ |
|---|---|---|---|---|
| 56 | diphenylamino | —OH | H | —OH |
| 57 | H | octahydroazocin-1-yl | acetyl | acetoxy |
| 58 | —OH | octahydroazocin-1-yl | H | —OH |

The derivatives of this invention inhibit the growth of pathogenic bacteria, especially gram-positive bacteria, and Mycoplasma species. Certain of the derivatives are active against some gram-negative bacteria, such as Pasteurella species. The minimal inhibitory concentrations (MIC's) at which illustrative compounds inhibit certain bacteria are given in Tables II and III. The MIC's in Table II were determined by standard agar-dilution assays. The MIC's in Table III were obtained using a conventional broth-dilution microtiter test.

TABLE II

Antibiotic Activity of Formula 1 Compounds[a]

| Test Organism | Test Compound[b] | | | | | | | | | | | | | | |
|---|---|---|---|---|---|---|---|---|---|---|---|---|---|---|---|
|  | 1 | 2 | 3 | 4 | 5 | 6 | 16 | 17 | 22 | 25 | 26 | 30 | 31 | 32 | 33 | 34 |
| *Staphylococcus aureus* X1.1 | 1 | 32 | 32 | 8 | 4 | 4 | 16 | 64 | 8 | 4 | 64 | 0.25 | 4 | 1 | 1 | 0.25 |
| *Staphylococcus aureus* V41[c] | 1 | 32 | 64 | 16 | 8 | 8 | 32 | 64 | 8 | 4 | 32 | 0.25 | 4 | 1 | 1 | 0.25 |
| *Staphylococcus aureus* X400[d] | 2 | 64 | 128 | 32 | 16 | 16 | 64 | 64 | 32 | 4 | 64 | 0.5 | 16 | 2 | 2 | 0.5 |
| *Staphylococcus aureus* S13E | 1 | 32 | 64 | 8 | 8 | 8 | 32 | 64 | 8 | 8 | 64 | 0.25 | 4 | 1 | 1 | 0.25 |
| *Staphylococcus epidermidis* EPI1 | 0.5 | 16 | 32 | 4 | 4 | 4 | 16 | 32 | 8 | 4 | 64 | 0.25 | 4 | 1 | 1 | 0.25 |
| *Staphylococcus epidermidis* EPI2 | 1 | 64 | 64 | 32 | 16 | 2 | 64 | 32 | 4 | 4 | 32 | 0.5 | NT | 1 | 1 | 0.12 |
| *Streptococcus pyogenes* C203 | 1 | 32 | 128 | 4 | 2 | NT[h] | 8 | 128 | NT | 2 | 64 | 0.25 | 16 | 2 | 2 | 0.12 |
| *Streptococcus pneumoniae* Park I | 0.5 | 32 | 16 | 2 | 1 | 2 | 4 | 16 | 4 | 1 | 8 | 0.12 | 2 | 0.25 | 0.5 | 0.12 |
| Streptococcus Group D X66 | 2 | —[g] | — | 16 | 8 | 16 | 32 | — | 16 | 8 | 128 | 0.5 | 8 | 0.5 | 1 | 2 |
| Streptococcus Group 9960 | 2 | — | — | 32 | 16 | 16 | 32 | — | 16 | 8 | — | 0.5 | 16 | 2 | 2 | 2 |
| *Haemophilus influenzae* C.L.[e] | 16 | 16 | 128 | 2 | 8 | 64 | 64 | — | 128 | 64 | — | NT | — | — | 128 | 4 |
| *Haemophilus influenzae* 76[f] | 16 | 32 | 128 | 2 | 8 | 64 | 16 | — | 128 | NT | — | NT | — | — | — | 8 |
| *Escherichia coli* EC14 | 64 | — | — | 128 | 64 | — | — | — | — | — | — | —[g] | — | — | — | — |
| *Escherichia coli* TEM | 16 | 128 | 128 | 8 | 8 | 64 | — | — | 128 | — | — | 8 | — | — | — | 8 |
| *Klebsiella pneumoniae* X26 | 4 | 16 | 64 | 8 | 4 | 16 | 128 | — | 32 | 64 | — | 8 | — | — | 32 | 8 |
| *Klebsiella pneumoniae* KAE | —[g] | — | — | — | — | — | — | — | — | — | — | — | — | — | — | — |

| Test Organism | 38 | 40 | 41 | 42 | 43 | 44 | 45 | 46 | 47 | 52 | 58 | 54 | 55 | 56 |
|---|---|---|---|---|---|---|---|---|---|---|---|---|---|---|
| *Staphylococcus aureus* X1.1 | 64 | 4 | 0.5 | 1 | 0.5 | 1 | 8 | 1 | 0.25 | 0.5 | 0.5 | 2 | 8 | 4 |
| *Staphylococcus aureus* V41[c] | 16 | 4 | 0.5 | 0.5 | 0.5 | 1 | 16 | 0.5 | 0.25 | 0.5 | 0.5 | 2 | 8 | 2 |
| *Staphylococcus aureus* X400[d] | 64 | 16 | 0.5 | 1 | 1 | 2 | 32 | 2 | 0.25 | 1 | 1 | 2 | 8 | 4 |
| *Staphylococcus aureus* S13E | 32 | 4 | 0.5 | 1 | 0.5 | 1 | 8 | 1 | 0.25 | 0.5 | 0.5 | 2 | 4 | 2 |
| *Staphylococcus epidermidis* EPI1 | 32 | 4 | 0.5 | 0.5 | 0.5 | 1 | 8 | 1 | 0.25 | 0.5 | 0.5 | 2 | 4 | 2 |
| *Staphylococcus epidermidis* EPI2 | 16 | 4 | 0.5 | 1 | 0.25 | 0.5 | 2 | 0.25 | 0.25 | 0.5 | 0.25 | 2 | 2 | 1 |
| *Streptococcus pyogenes* C203 | — | 16 | 0.5 | 1 | 0.12 | 4 | 32 | 2 | 0.25 | 0.25 | 0.25 | 1 | 2 | 2 |
| *Streptococcus pneumoniae* Park I | 16 | 4 | 0.25 | 0.12 | 1 | 0.5 | 2 | 0.5 | NT | 0.25 | 0.25 | 0.5 | 1 | 1 |
| Streptococcus Group D X66 | — | 8 | 1 | 0.5 | 1 | 2 | 64 | 2 | 0.25 | 1 | 2 | 4 | 8 | 4 |
| *Streptococcus pyogenes* 9960 | — | 8 | 1 | 1 | 2 | 2 | 128 | 4 | 0.25 | 2 | 4 | 4 | 8 | 8 |
| *Haemophilus influenzae* C.L.[e] | — | NT | 8 | 16 | 4 | 16 | 32 | 16 | 32 | 8 | 2 | NT | NT | 32 |
| *Haemophilus influenzae* 76[f] | — | NT | 8 | 16 | 8 | 16 | 64 | 16 | 16 | 8 | 4 | NT | NT | 16 |
| *Escherichia coli* EC14 | — | — | 128 | — | — | — | — | — | — | 64 | 64 | — | — | — |
| *Escherichia coli* TEM | — | — | 16 | — | 16 | — | — | 128 | 128 | 8 | 8 | 16 | — | — |
| *Klebsiella pneumoniae* X26 | — | 16 | 4 | 16 | 4 | 32 | 16 | 4 | 4 | 4 | 2 | 4 | — | NT |

TABLE II-continued

Antibiotic Activity of Formula 1 Compounds[a]

| | | | | | | | | | | | | | | |
|---|---|---|---|---|---|---|---|---|---|---|---|---|---|---|
| *Klebsiella pneumoniae* KAE | — | — | — | — | — | — | — | — | — | — | 64 | — | — | — |

[a]MIC in mcg/ml
[b]Compound numbers from Table I
[c]Penicillin-resistant strain
[d]Methicillin-resistant strain
[e]Ampicillin-sensitive strain
[f]Ampicillin-resistant strain
[g]Compound not active at 128 mcg/ml
[h]NT = not tested

TABLE III

Antibiotic Activity of Formula 1 Compounds[a]

| Test Organism | 1 | 2 | 3 | 4 | 5 | 6 | 16 | 17 | 22 | 25 | 26 | 30 | 31 | 32 | 33 |
|---|---|---|---|---|---|---|---|---|---|---|---|---|---|---|---|
| *Staphylococcus aureus* | 3.12 | 50 | 50 | 12.5 | 6.25 | 25 | 12.5 | — | 25 | 12.5 | — | 1.56 | 12.5 | 0.39 | 0.78 |
| *Streptococcus sp.* 80 | 3.12 | 25 | 50 | 6.25 | 1.56 | 3.12 | 12.5 | 50 | 6.25 | 6.25 | — | 0.39 | 12.5 | .048 | 0.097 |
| *Pasteurella multocida* 17E[c] | 12.5 | 25 | 50 | 3.12 | 3.12 | 50 | — | — | 50 | — | — | 12.5 | —[f] | 3.12 | 3.12 |
| *Pasteurella multocida* 60A[d] | 25 | 25 | 50 | 3.12 | 3.12 | 50 | — | — | 50 | 50 | — | 6.25 | — | 3.12 | 3.12 |
| *Pasteurella multocida* 22A | 25 | 25 | 50 | 12.5 | 6.25 | 50 | — | — | 50 | — | — | 6.25 | — | 3.12 | 3.12 |
| *Pasteurella multocida* 40G | 25 | 50 | 50 | 6.25 | 6.25 | 50 | 50 | — | 50 | 50 | — | 6.25 | — | 3.12 | 3.12 |
| *Pasteurella multocida* 68C | 6.25 | 12.5 | 25 | 3.12 | 1.56 | 25 | — | — | 25 | 50 | — | 6.25 | — | 3.12 | 3.12 |
| *Pasteurella hemolytica* 22C | 25 | 50 | 50 | 6.25 | 6.25 | 50 | — | — | 50 | — | — | 6.25 | — | 12.5 | 25 |
| *Pasteurella hemolytica* 41D | 12.5 | 50 | 50 | 6.25 | 3.12 | 50 | — | — | 50 | — | — | 6.25 | — | 12.5 | 25 |
| *Pasteurella hemolytica* 23C | 12.5 | 50 | 50 | 6.25 | 3.12 | 50 | — | — | 50 | — | — | 6.25 | — | 12.5 | 25 |
| *Mycoplasma gallisepticum* | 3.12 | 50 | 50 | 3.12 | 1.56 | 3.12 | 6.25 | 12.5 | 0.78 | 1.56 | 12.5 | 0.78 | 12.5 | 0.78 | 0.78 |
| *Mycoplasma gallisepticum* 34159[e] | 6.25 | — | — | 50 | 50 | 50 | — | 50 | 50 | — | 50 | 12.5 | 25 | 6.25 | 12.5 |
| *Mycoplasma gallisepticum* 41313[e] | 50 | 50 | c[g] | 50 | 50 | 50 | — | 50 | 50 | — | 50 | 50 | 25 | 25 | 25 |
| *Mycoplasma synoviae* | 50 | — | 25 | 12.5 | 3.12 | NT | 6.25 | NT | NT | 50 | NT | 6.25 | NT | 6.25 | 6.25 |
| *Mycoplasma hyorhinis* | —[f] | 50 | — | 50 | — | 50 | — | 50 | 25 | — | 50 | 50 | 50 | 50 | 50 |

| Test Organism | 34 | 38 | 40 | 41 | 42 | 43 | 44 | 45 | 46 | 47 | 54 | 55 | 57 | 58 |
|---|---|---|---|---|---|---|---|---|---|---|---|---|---|---|
| *Staphylococcus aureus* | 0.39 | 25 | 6.25 | 0.78 | 1.56 | 0.39 | 1.56 | 12.5 | 1.56 | 3.12 | 0.78 | 0.78 | 0.39 | 0.78 |
| *Streptococcus sp.* 80 | 0.78 | 50 | 12.5 | 1.56 | 1.56 | 0.78 | 3.12 | 1.56 | 3.12 | 1.56 | 3.12 | 1.56 | 0.195 | 1.56 |
| *Pasteurella multocida* 17E[c] | 3.12 | — | 25 | 12.5 | 25 | 0.78 | 50 | 25 | 12.5 | 25 | 12.5 | — | 1.56 | 3.12 |
| *Pasteurella multocida* 60A[d] | 6.25 | — | 12.5 | 3.12 | 12.5 | 0.78 | 25 | 12.5 | 12.5 | 25 | 6.25 | 50 | 1.56 | 0.78 |
| *Pasteurella multocida* 22A | 6.25 | — | 25 | 25 | 25 | 1.56 | 50 | 12.5 | 12.5 | 50 | 25 | — | 1.56 | 1.56 |
| *Pasteurella multocida* 40G | 3.12 | — | 25 | 12.5 | 25 | 1.56 | 25 | 12.5 | 12.5 | 12.5 | 25 | — | 1.56 | 0.39 |
| *Pasteurella multocida* 68C | 3.12 | — | 12.5 | 3.12 | 25 | 1.56 | 25 | 12.5 | 6.25 | 12.5 | 6.25 | — | 0.78 | 1.56 |
| *Pasteurella hemolytica* 22C | 1.56 | — | 50 | 12.5 | 25 | 0.78 | — | 25 | 50 | 25 | 12.5 | — | 0.78 | 0.78 |
| *Pasteurella hemolytica* 41D | 3.12 | — | 50 | 12.5 | 25 | 1.56 | — | 25 | 25 | 25 | 12.5 | — | 0.78 | 0.39 |
| *Pasteurella hemolytica* 23C | 3.12 | — | 50 | 12.5 | 25 | 1.56 | — | 25 | 50 | 25 | 12.5 | — | 1.56 | 0.78 |
| *Mycoplasma gallisepticum* | 0.097 | 50 | 6.25 | 3.12 | 6.25 | 0.78 | 3.12 | 6.25 | 1.56 | 1.56 | 0.048 | 0.097 | 0.78 | 0.39 |
| *Mycoplasma gallisepticum* 34159[e] | 50 | 50 | — | 50 | 25 | — | 12.5 | — | 50 | 50 | 3.12 | 3.12 | 50 | — |
| *Mycoplasma gallisepticum* 41313[e] | 25 | 50 | — | 50 | 25 | — | 12.5 | 50 | 50 | 50 | 0.78 | 0.78 | 50 | 50 |
| *Mycoplasma galisepticum synoviae* | 12.5 | NT | NT | 3.12 | 6.25 | — | 12.5 | 12.5 | 6.25 | 6.25 | 25 | 6.25 | 12.5 | 6.25 |
| *Mycoplasma hyorhinis* | 50 | 50 | 50 | 50 | 25 | 50 | 50 | — | 25 | 25 | 50 | 50 | — | 25 |

[a]MIC in mcg/ml
[b]Compound numbers from Table I
[c]Bovine isolate
[d]Avian isolate
[e]Resistant strain
[f]MIC greater than 50 mcg/ml
[g]contaminated Some of the derivatives of this invention have shown in vivo antimicrobial activity against experimentally-induced infections in laboratory animals. When two doses of test compound were administered to mice experimentally infected with *S. pyogenes* C203, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for illustrative compounds are given in Table IV.

TABLE IV

$ED_{50}$ Values of Illustrative Formula 1 Compounds[a]

| | *Streptococcus pyogenes* C203 | |
|---|---|---|
| Test Compound[b] | Subcutaneous | Oral |
| 1 | >30 | >100 |
| 4 | 16.1 | >100 |
| 5 | 7.2 | >100 |
| 16 | 10.4 | 88 |
| 25 | >25 | >100 |
| 30 | >30 | >100 |
| 32 | >10 | >50 |
| 33 | >10 | >50 |
| 41 | >25 | >100 |
| 42 | >25 | 78 |
| 43 | >12.5 | >100 |
| 44 | >10 | >50 |
| 45 | >10 | >100 |
| 46 | >10 | >100 |
| 47 | >10 | >50 |

[a]mg/kg × 2; doses given 1 and 4 hours post-infection
[b]Compound numbers from Table I.

Certain of the formula 1 compounds of this invention have also shown in vivo activity against infections induced by gram-negative bacteria. Table V summarizes the results of tests in which illustrative compounds were evaluated against a Pasteurella infection in one-day old chicks. The compounds were administered parenterally after challenge of the chicks with *Pasteurella multocida* (0.1 ml of a $10^{-4}$ dilution of a twenty-hour tryptose broth culture of an avian *P. multocida* given subcutaneously). In these tests, unless indicated otherwise, all non-medicated infected chicks died within 24 hours of Pasteurella challenge. In the tests summarized in Table V, the compounds were administered by subcutaneous injection at a dosage of 30 mg/kg, 1 and 4 hours post-challenge of the chicks with *P. multocida*.

TABLE V

Activity of Formula 1 Compounds Administered Subcutaneously to *Pasteurella multocida*-Infected Chicks[a]

| Test Compound[b] | Number of Deaths/Number Treated |
|---|---|
| 1 | 9/10 |
| 4 | 1/10 |
| 5 | 1/10 |
| 30 | 9/10 |
| 34 | 10/10 |
| 43 | 8/10 |
| 45 | 10/10 |
| 46 | 10/10 |

[a] Administered subcutaneously; 30 mg/kg × 2
[b] Compound numbers from Table I

The compounds which are preferred for in vivo activity against gram-positive microorganisms are those formula 1 compounds wherein R is $-N(R^6)_2$. Another preferred group are the formula 1 compounds wherein $R^1$ is $-OH$ or $-OAr$ and Ar is a group (iii) substituent. Still another group of compounds preferred for in vitro activity against gram-positive bacteria and for activity against Mycoplasma species are the formula 1 compounds wherein $R^1$ is a group (iii) substituent.

This invention also relates to methods of controlling infections caused by gram-positive bacteria and Mycoplasma species. In carrying out the methods of this invention, an effective amount of a specified formula 1 compound is administered parenterally to an infected or susceptible warm-blooded animal.

The dose which is effective to control the infection will vary with the severity of the infection and the age, weight, and condition of the animal. The total dose required for protection parenterally will generally, however, be in the range of from about 1 to about 100 mg/kg and preferably will be in the range of from about 1 to about 50 mg/kg. Suitable dosage regimens can be constructed.

In another aspect, this invention relates to compositions useful for the control of infections caused by gram-positive bacteria and Mycoplasma species. These compositions comprise a specified compound of formula 1 together with a suitable vehicle. Compositions may be formulated for parenteral administration by methods recognized in the pharmaceutical art.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided:

Preparation 1

2',4'-Di-O-acetyl-20-dihydro-OMT

20-Dihydro-OMT (3.1 g, 5.2 mmol) was dissolved in acetone (100 ml) and was treated over a five-minute period with acetic anhydride (2.0 ml, 21.2 mmol). After stirring for nine hours at room temperature, the reaction mixture was quenched into saturated sodium bicarbonate solution (500 ml) and the product was extracted into dichloromethane (2×250 ml). The combined dichloromethane extracts were dried (sodium sulfate) and filtered and the filtrate was evaporated under reduced pressure. The residue was dried in vacuo overnight to yield 3.4 g (96%) of 2',4'-di-O-acetyl-20-dihydro-OMT.

Preparation 2

23-Iodo-20,23-dideoxy-20-dihydro-OMT

20-Deoxy-20-dihydro-OMT (2.0 g, 3.4 mmol), tetrabutylammonium iodide (3.8 g, 10.3 mmol) and s-collidine (1.36 ml, 10.3 mmol) were dissolved in dichloromethane (40 ml). The solution was cooled to $-78°$ under an argon atmosphere and then was treated dropwise with triflic anhydride (0.7 ml). After 5 minutes at $-78°$, the cooling bath was removed and the solution was stirred for 30 minutes at room temperature. Since tlc[a] analysis showed unreacted starting material was still present, the solution was cooled to $-78°$ again and then treated with additional triflic anhydride (0.03 ml). The cooling bath was again removed and the reaction was stirred at room temperature for 30 minutes. The solution was extracted with saturated sodium bicarbonate solution, dried ($Na_2SO_4$) and filtered. The filtrate was evaporated to dryness and the crude product was purified by flash chromatography on silica gel, eluting with a linear gradient of dichloromethane (1 L) and 5% methanol in dichloromethane (1 L). Fractions containing the desired product were located by tlc analysis, combined and evaporated under reduced pressure to yield 2.0 g of 23-iodo-20,23-dideoxy-20-dihydro-OMT.
[a] thin layer chromatography

EXAMPLE 1

2',4'-Di-O-acetyl-20-O-phenylacetyl-20-dihydro-OMT
and
2',4'-di-O-acetyl-20,23-di-O-phenylacetyl-20-dihydro-OMT 2',4'-Di-O-acetyl-20-dihydro-OMT (3.0 g, 4.4 mmol) was dissolved in dichloromethane (50 ml) and pyridine (2 ml). The solution was cooled to −78° and treated dropwise with phenylacetyl chloride (0.725 ml, 5.5 mmol) over a 2-minute period with vigorous stirring. After 15 minutes at −78°, the cooling bath was removed and the solution was stirred at room temperature for six hours. The solution was then poured into saturated sodium bicarbonate solution (100 ml) and the product was extracted into dichloromethane (2×50 ml). The combined dichloromethane extracts were dried (sodium sulfate) and filtered and the filtrate was evaporated. The residue (4 g) was separated on a Waters Prep 500 chromatograph, eluting with a linear gradient of toluene (4 L) and ethyl acetate (4 L). Fractions containing the desired products were located by tlc analysis, combined and evaporated under reduced pressure to yield 2.3 g of 2',4'-di-O-acetyl-20-O-phenylacetyl-20-dihydro-OMT and 0.6 g of 2',4'-di-O-acetyl-20,23-di-O-phenylacetyl-20-dihydro-OMT.

EXAMPLE 2

20-O-Phenylacetyl-20-dihydro-OMT

2',4'-Di-O-acetyl-20-O-phenylacetyl-20-dihydro-OMT (1.2 g, 1.5 mmol) was dissolved in methanol (80 ml) and water (20 ml) and the solution was refluxed for 1.5 hr. After cooling to room temperature, solvent was evaporated under reduced pressure and the residue was dissolved in dichloromethane (50 ml), dried (sodium sulfate) and filtered. Evaporation of the filtrate yielded 0.92 g of 20-O-phenylacetyl-20-dihydro-OMT.

EXAMPLE 3

20,23-Di-O-Phenylacetyl-20-dihydro-OMT

In a manner similar to that of Example 2, 2',4'-di-O-acetyl-20,23-di-O-phenylacetyl-20-dihydro-OMT (0.48 g) was hydrolyzed to yield 0.44 g of 20,23-di-O-phenylacetyl-20-dihydro-OMT.

EXAMPLE 4

20-N-Methylamino-20-deoxy-20-dihydro-OMT

OMT (1.2 g) and methylamine hydrochloride (1.36 g) were dissolved in dry methanol (40 ml). After stirring for one hour at room temperature, sodium cyanoborohydride (500 mg) was added. The solution was stirred for 3 hours and then was poured into saturated sodium bicarbonate solution (200 ml). The product was extracted into dichloromethane (2×200 ml) and the combined extracts were dried (Na2SO4) and filtered. The filtrate was evaporated and the residue (0.9 g) was dissolved in dichloromethane and separated by flash chromatography on silica gel (Grace 60), eluting with a linear gradient of 1 liter of dichloromethane-methanol-conc. ammonium hydroxide (90:10:0.5) and 1 liter of dichloromethane-methanol-conc. ammonium hydroxide (75:25:0.5). Fractions containing the desired product were located by tlc analysis, combined and evaporated under reduced pressure to yield 0.14 g of the title compound.

EXAMPLE 5

20-N-Benzylamino-20-deoxy-20-dihydro-OMT

Using a procedure like that of Example 4, OMT (2.2 g) and benzylamine (4.1 ml) in methanol (60 ml) were treated with sodium cyanoborohydride (1.0 g). After extractive workup, the crude product was purified by silica gel chromatography on a Waters Prep 500 instrument, eluting with a linear gradient of dichloromethane (4 L) and dichloromethane-methanol-conc. ammonium hydroxide (90:10:0.5, 4 L), to yield 0.21 g of the title compound.

EXAMPLE 6

20-N-Dimethylamino-20-deoxy-20-dihydro-OMT

Using a procedure like that of Example 4, OMT (1.2 g) and dimethylamine hydrochloride (1.6 g) in methanol (40 ml) were treated with sodium cyanoborohydride (0.5 g). After extractive workup and purification by silica gel chromatography as described in example 5, 0.61 g of the title compound was obtained.

EXAMPLE 7

20-N-Benzylamino-20-deoxy-20-dihydro-DMOT

Using a procedure like that of Example 4, DMOT (1.56 g) and benzylamine (4.0 ml) in methanol (60 ml) were treated with sodium cyanoborohydride (1 g). After extractive workup, the crude product was purified by flash chromatography on silica gel, eluting with a linear gradient of dichloromethane (1 L) and dichloromethane-methanol (3:1, 1 L) to yield 0.24 g of the title compound.

EXAMPLE 8

20-N-Phenethylamino-20-deoxy-20-dihydro-DMT

DMT (10.4 g) and phenethylamine (2.8 ml) were dissolved in dry methanol (420 ml) and the solution was stirred for 30 minutes at room temperature. Sodium cyanoborohydride (3.5 g) was added and the solution was stirred for 2.5 hours. The solution was poured into saturated sodium bicarbonate solution (1 l) and the product was extracted into dichloromethane (4×500 ml). The combined extracts were dried (Na2SO4) and filtered and the filtrate was evaporated. The residue was dissolved in a small volume of dichloromethane and separated by flash chromatography on silica gel, eluting with a linear gradient of dichloromethane-methanol-conc. ammonium hydroxide (1 L of 125:1:0.1 to 1 L of 100:10:1) followed by an additional 1 L of the latter solvent mixture. Fractions containing the desired product were located by tlc analysis, combined and evaporated to yield 2.8 g of the title compound.

EXAMPLE 9

20-N-Phenethylamino-20-deoxy-20-dihydro-OMT

20-N-Phenethylamino-20-deoxy-20-dihydro-DMT (1.5 g) was dissolved in 1N sulfuric acid (60 ml) and stirred for 1 hour at room temperature. The solution was slowly poured into saturated sodium bicarbonate solution (500 ml) and the product was extracted into dichloromethane (3×300 ml). The combined extracts were dried (Na2SO4) and filtered and the filtrate was evaporated under reduced pressure to yield 0.88 g of the title compound.

EXAMPLE 10

20,23-Di-N-phthalimido-20,23-dideoxy-20-dihydro-DMT

20-Dihydro-DMT (1.49 g, 2.0 mmol), triphenylphosphine (2.1 g, 8 mmol) and phthalimide (1.18 g, 8.0 mmol) were dissolved in tetrahydrofuran (50 ml) under an argon atmosphere. Diethyl azodicarboxylate (1.4 g, 8 mmol) was added dropwise and the solution was stirred for 30 minutes at room temperature. Methanol (about 1 ml) was added to decompose excess reagent and, after stirring for 10 minutes, the solution was evaporated under reduced pressure. The residue was partitioned between ethyl acetate and 0.1M acetic acid (100 ml each) and a few ml of petroleum ether were added to break the emulsion that formed. The aqueous layer was separated, made alkaline with solid sodium bicarbonate and extracted with dichloromethane. The organic extracts were dried ($Na_2SO_4$) and filtered and the filtrate was evaporated. The residue was dissolved in a small volume of dichloromethane and separated by flash chromatography on silica gel, eluting first with dichloromethane (300 ml) followed by a linear gradient of dichloromethane (1 L) and 9% methanol in dichloromethane (1 L). Fractions containing the desired product were located by tlc analysis, combined and evaporated to dryness to yield 0.17 g of the title compound.

EXAMPLE 11

20,23-Di-N-Phthalimido-20,23-dideoxy-20-dihydro-OMT 20,23-Di-N-phthalimido-20,23-dideoxy-20-dihydro-DMT (100 mg) was dissolved in 1N sulfuric acid (10 ml) and dioxane (3 ml) and stirred for 1 hr at room temperature. The reaction was then neutralized with solid sodium bicarbonate and extracted with dichloromethane twice. The combined extracts were dried ($Na_2SO_4$) and filtered and the filtrate was evaporated to dryness under reduced pressure and then dried in vacuo to yield the title compound.

EXAMPLE 12

20-N-Phthalimido-20-deoxy-20-dihydro-DMOT

20-Dihydro-DMOT (3.64 g, 5 mmol), triphenylphosphine (2.62 g, 10 mmol) and phthalimide (1.47 g, 10 mmol) were dissolved in tetrahydrofuran (40 ml) under a nitrogen atmosphere. The solution was treated dropwise with diethyl azodicarboxylate (1.58 ml, 10 mmol) and then stirred for 1 hr at room temperature. The excess reagant was quenched with methanol (25 ml) and the solution was evaporated under reduced pressure. The residue was dissolved in a small volume of dichloromethane and separated by flash chromatography on silica gel, eluting with dichloromethane (1 L) followed by a linear gradient of dichloromethane (1 L) and 5% methanol in dichloromethane (1 L). Fractions containing the desired product were located by tlc analysis, combined and evaporated to dryness to yield 2.44 g of the title compound.

EXAMPLE 13

20-N-Phthalimido-20-deoxy-20-dihydro-DMT

In a manner analogous to that of example 12, 20-dihydro-DMT (2.96 g), triphenylphosphine (2.0 g) and phthalimide (1.18 g) were dissolved in tetrahydrofuran (35 ml) and treated with diethyl azodicarboxylate (1.4 ml). Since tlc analysis of the reaction mixture after 30 minutes showed a significant amount of unreacted 20-dihydro-DMT in addition to a mono-substituted and a di-substituted derivative, additional phthalimide (296 mg), triphenylphosphine (523 mg) and diethyl azodicarboxylate (0.33 ml), were added. After stirring for an additional 0.5 hr at room temperature, the reaction was quenched with methanol and worked up as described in example 12 to yield, from chromatography on silica gel as described above, 0.79 g of 20-N-phthalimido-20-deoxy-20-dihydro-DMT along with 2.16 g of 20,23-di-N-phthalimido-20,23-dideoxy-20-dihydro-DMT.

EXAMPLE 14

20-N-Phthalimido-20-deoxy-20-dihydro-DOMT

20-N-Phthalimido-20-deoxy-20-dihydro-DMOT (1.0 g) was dissolved in 1N sulfuric acid (80 ml) and stirred for 1 hr at room temperature. The solution was slowly added to saturated sodium bicarbonate solution (500 ml) and then was extracted with dichloromethane (3 × 300 ml). The combined extracts were dried ($Na_2SO_4$) and filtered and the filtrate was evaporated under reduced pressure to yield 0.50 g of the title compound.

EXAMPLE 15

20-N-Phthalimido-20-deoxy-20-dihydro-OMT

20-N-Phthalimido-20-deoxy-20-dihydro-DMT (355 mg) was hydrolyzed in 1N sulfuric acid (50 ml) for 1 hr. After workup as described in example 14, 170 mg of the title compound was obtained.

EXAMPLE 16

20,23-Di-O-phenyl-20-dihydro-OMT

20-Dihydro-OMT (1 g, 1.7 mmol), triphenylphosphine (1.3 g, 5.1 mmol) and phenol (0.47 g, 5.1 mmol) were dissolved in tetrahydrofuran (30 ml) under a nitrogen atmosphere. The solution was cooled in an ice bath and treated with diethyl azodicarboxylate (0.89 g, 5.1 mmol) over a 2-minute period. The cooling bath was removed and the solution was stirred for 1 hr at room temperature. Methanol (10 ml) was added and, after stirring for 15 minutes, the solution was evaporated under reduced pressure. The residual oil was treated with toluene and the white insoluble material was filtered. The filtrate was evaporated and the residue was partitioned between dichloromethane and saturated sodium bicarbonate solution. The organic layer was separated, dried ($Na_2SO_4$) and filtered and the filtrate was evaporated. The residue was separated by flash chromatography on silica gel, eluting with mixtures of methanol-dichloromethane as follows: 400 ml of 0%, 250 ml of 2%, 250 ml of 3%, 500 ml of 4% and 250 ml each of 6%, 8%, 10% and 16% methanol in dichloromethane. Fractions containing the desired product were located by tlc analysis, combined and evaporated to yield 144 mg of 20,23-di-O-phenyl-20-dihydro-OMT.

EXAMPLE 17

20-Dihydro-23-O-phenylpropionyl-OMT

23-O-Phenylpropionyl-OMT (1.9 g, 2.6 mmol) was dissolved in 1:1 isopropanol:water (30 ml). Sodium borohydride (0.025 g, 0.65 mmol) was added to this solution and the reaction was stirred for 0.5 hr. The pH of the reaction was adjusted from pH 10.5 to pH 7.0 with 1N sulfuric acid. The solution was concentrated to aqueous under reduced pressure and saturated NaH- CO₃ solution was added. The product was extracted into dichloromethane and the extracts were dried (Na₂SO₄) and filtered. The filtrate was evaporated under reduced pressure to yield 1.75 g (92%) of the title compound as a white foam.

EXAMPLE 18

20-Dihydro-23-Octahydroazocin-1-yl-23-deoxy-OMT

23-Octahydroazocin-1-yl-OMT (900 mg, 1.3 mmol) was reduced with sodium borohydride (12 mg, 0.33 mmol) in 1:1 isopropanol-water (15 ml) as described in example 17, yielding 815 mg (90%) of the 20-dihydro derivative.

EXAMPLE 19

20-O-Phenyl-20-dihydro-23-O-phenylpropionyl-OMT

20-Dihydro-23-O-phenylpropionyl-OMT (1.7 g, 2.3 mmol), triphenylphosphine (1.2 g, 4.6 mmol) and phenol (0.43 g, 4.6 mmol) were dissolved in tetrahydrofuran (45 ml) under a nitrogen atmosphere. The solution was cooled in an ice bath and then was treated dropwise with diethyl azodicarboxylate (0.8 g, 4.6 mmol). After 5 minutes, the cooling bath was removed and the solution was stirred for 2 hr at room temperature. Since tlc analysis of the reaction indicated the presence of unreacted starting material, one-half of the initial amounts (2.3 mmol) of triphenylphoshine, phenol and diethyl azodicarboxylate were each added. After stirring for another 30 minutes, methanol (10 ml) was added to decompose excess reagent and the solution was evaporated under reduced pressure. The residual oil was treated with toluene and the insoluble material was filtered. The filtrate was evaporated under reduced pressure and the residue was separated by flash chromatography on silica gel, eluting step-wise with mixtures of methanol-dichloromethane as follows: 400 ml of 0%, 250 ml of 2%, 250 ml. of 4%, 750 ml of 6% and 250 ml of 8% methanol in dichloromethane. Fractions containing the desired product were located by tlc analysis, combined and evaporated under reduced pressure to yield 0.26 g of 20-O-phenyl-20-dihydro-23-O-phenylpropionyl-OMT.

EXAMPLE 20

20-O-Phenyl-20-dihydro-23-Octahydroazocin-1-yl-OMT

20-Dihydro-23-octahydroazocin-1-yl-OMT (800 mg, 1.2 mmol), triphenylphosphine (940 mg, 3.6 mmol) and phenol (340 mg, 3.6 mmol) were dissolved in tetrahydrofuran (20 ml). The solution was treated with diethyl azodicarboxylate (630 mg, 3.6 mmol), stirred for 1 hour, and worked up as described in example 19. The crude product was purified by flash chromatography on silica gel, eluting stepwise with mixtures of methanoldichloromethane as follows: 400 ml of 0%, 250 ml of 2%, 500 ml of 3%, 250 ml each of 4%, 6%, 8%, 12% and 16% methanol in dichloromethane. Fractions containing the desired product were located by tlc analysis, combined and evaporated to yield 90 mg of the title compound.

EXAMPLE 21

2',4',23-Tri-O-acetyl-20-deoxy-20-dihydro-OMT

20-Deoxy-20-dihydro-OMT (5 g) was dissolved in pyridine (70 ml). The solution was treated with acetic anhydride (4 ml) and then was stirred overnight at room temperature. The solution was evaporated under reduced pressure and the residue was dissolved in dichloromethane and cyclohexane and then re-evaporated to remove most of the pyridine. The residue was dissolved in dichloromethane, extracted with saturated sodium bicarbonate solution, dried (Na₂SO₄) and filtered. The filtrate was evaporated to dryness and the residue was redissolved and re-evaporated to remove pyridine as before and finally was suspended in hexane and filtered. The solid residue (5.3 g) was separated on a Waters Prep 500 chromatography over silica gel, eluting with a linear gradient of toluene (1 L) and toluene-ethyl acetate (1:3, 1 L). Fractions containing the desired product were located by tlc analysis, combined and evaporated to dryness to yield 3.72 g of 2', 4', 23-tri-O-acetyl-20-deoxy-20-dihydro-OMT.

EXAMPLE 22

23-O-Phenylacetyl-20-deoxy-20-dihydro-OMT

20-Deoxy-20-dihydro-OMT (2 g, 3.4 mmol) was dissolved in dichloromethane (40 ml) and pyridine (0.55 ml). The solution was cooled to −78° and treated with phenylacetyl chloride (0.55 ml, 4.1 mmol). The cooling bath was removed and the reaction was allowed to warm to room temperature and then stirred for an additional 0.5 hr at room temperature. Since tlc analysis of the reaction showed the presence of starting material, the solution was again cooled to −78° and treated with additional phenylacetyl chloride (0.35 ml). Sequence was repeated again, using 0.08 ml of phenylacetyl chloride the final time. The final reaction mixture was extracted with saturated sodium bicarbonate solution, dried (Na₂SO₄) and filtered and the filtrate was evaporated to dryness. The residue was separated by flash chromatography on silica gel, eluting with a linear gradient of dichloromethane (1 L ) and 20% methanol in dichloromethane (1 L). Fractions containing the desired product were identified by tlc analysis, combined and evaporated to yield the title compound.

EXAMPLE 23

23-Phenylthio-20,23-dideoxy-20-dihydro-OMT

20-Deoxy-20-dihydro-OMT (3.0 g, 5.15 mmol) was dissolved in dichloromethane (40 ml) and s-collidine (1.36 ml). The solution was cooled to −78° and treated with triflic anhydride (1.0 ml initially, then 0.3 ml additionally); thiophenyl (1.25 ml) was added at −78° and the mixture was stirred at −78° for 1.5 hr. The reaction was stirred for another 2.5 hr while warming to room temperature and then was extracted with saturated sodium bicarbonate solution, dried (Na₂SO₄) and filtered. The filtrate was evaporated and the residue was washed with hexane and then separated by flash chromatography on silica gel, eluting with a linear gradient of dichloromethane (1 L) and 20% methanol in dichloromethane (1 L). Fractions containing the desired product were located by tlc analysis, combined and evaporated to yield 700 mg of the title compound.

EXAMPLE 24

23-Octahydroazocin-1-yl-20,23-dideoxy-20-dihydro-OMT

23-Iodo-20,23-dideoxy-20-dihydro-OMT (69 mg) and heptamethyleneimine (0.05 ml) were dissolved in acetonitrile (2 ml) and the solution was refluxed for 2 hr under an argon atmosphere. The solution was cooled to room temperature and poured into saturated sodium bicarbonate solution (10 ml). The product was extracted into dichloromethane and the extracts were dried (Na$_2$SO$_4$) and filtered. The filtrate was evaporated and the residue was separated by preparative tlc on a 20×20 cm, 2 mm thick plate of silica gel (E. Merck), developing with dichloromethane-methanol-conc. ammonium hydroxide (90:10:2). The band on the silica gel plate was located by UV light and was scraped from the plate, dried in vacuo to remove solvent and then eluted with dichloromethane-methanol (1:1, 50 ml) for 45 minutes. The mixture was filtered and the filtrate was evaporated to dryness to yield 65 mg of the title compound.

EXAMPLE 25

23-(4-Hydroxypiperidino)-20,23-dideoxy-20-dihydro-OMT

23-Iodo-20,23-dideoxy-20-dihydro-OMT (1.1 g, 1.6 mmol) and 4-hydroxypiperidine (0.32 g 3.2 mmol) were dissolved in acetonitrile (20 ml) and refluxed under an argon atmosphere for 2 hr. Additional 4-hydroxypiperidine (300 mg) was added to consume unreacted starting material and the solution was refluxed for an additional 3 hr. The solution was cooled to room temperature and then evaporated under reduced pressure. The residue was dissolved in dichloromethane, extracted with saturated sodium bicarbonate solution, dried (Na$_2$SO$_4$) and filtered. The filtrate was evaporated and the residue was purified by flash chromatography on silica gel, eluting with a linear gradient of dichloromethane (1 L) and 12% methanol in dichloromethane (1 L). Fractions containing the desired product were located by tlc analysis, combined and evaporated to yield 865 mg of the title compound.

EXAMPLE 26

23-O-(2,3-Dimethoxyphenyl)-20-deoxy-20-dihydro-OMT

20-Deoxy-20-dihydro-OMT (3.0 g, 5.15 mmol), triphenylphosphine (2.7 g, 10.3 mmol) and 2,3-dimethoxyphenol (1.59 g, 10.3 mmol) were dissolved in tetrahydrofuran (150 ml) under an argon atmosphere. The solution was treated with diethyl azodicarboxylate (1.7 ml, 10.3 mmol) and then was stirred for 40 minutes at room temperature. Methanol (2 ml) was added to decompose excess reagent and the solution was evaporated to dryness under reduced pressure. The residue was taken up in toluene and the insoluble material was filtered. The filtrate was extracted with saturated sodium bicarbonate solution, dried (Na$_2$SO$_4$) and filtered and the filtrate was evaporated to dryness. The residue was purified by chromatography on silica gel (Waters Prep 500), eluting with dichloromethane (2 L) followed by a linear gradient of dichloromethane (2 L) and 10% methanol in dichloromethane (2 L); the column was finally eluted with 2 L of the latter solvent. Fractions containing the desired product were located by tlc analysis, combined and evaporated to yield 2.06 g (54%) of the title compound.

EXAMPLE 27

23-O-(3-Pyridyl)-20-deoxy-20-dihydro-OMT

20-Deoxy-20-dihydro-OMT (3.0 g, 5.15 mmol), triphenylphosphine (2.7 g, 10.3 mmol) and 3-hydroxypyridine (979 mg, 10.3 mmol) were dissolved in tetrahydrofuran (50 ml) under an argon atmosphere and treated with diethyl azodicarboxylate (1.7 ml, 10.3 mmol). After workup and chromatography as described in example 26, 0.63 g of the title compound was obtained.

EXAMPLE 28

23-O-(m-Dimethylaminophenyl)-20-deoxy-20-dihydro-OMT

20-Deoxy-20-dihydro-OMT (3.0 g, 5.15 mmol), triphenylphosphine (2.7 g, 10.3 mmol) and m-dimethylaminophenol (1.4 g, 10.3 mmol) were dissolved in tetrahydrofuran (50 ml) under an argon atmosphere. Diethyl azodicarboxylate (1.7 ml, 10.3 mmol) was added and the solution was stirred for 1 hr at room temperature. Since starting material had not been consumed at this point, additional triphenylphosphine (1.35 g), m-dimethylaminophenol (0.70 g) and diethyl azodicarboxylate (0.85 ml) were added and the solution was stirred for another 0.5 hr. MeOH (about 3 ml) was then added to quench the reaction and the solution was evaporated under reduced pressure. The residue was worked up as described in example 26 and purified by chromatography on silica gel (Waters Prep 500), eluting with dichloromethane (2 L) followed by a linear gradient of dichloromethane (4 L) and 15% methanol in dichloromethane (4 L). Fractions containing the desired product were located by tlc analysis, combined and evaporated to dryness to yield 1.12 g of the title compound as a purple glassy solid.

EXAMPLE 29

20-Diphenylamino-20-deoxy-20-dihydro-OMT

OMT (3.0 g, 5 mmol) was dissolved in dimethylformamide (10 ml) and the solution was diluted with toluene (100 ml). Diphenylamine (1.69 g, 10 mmol) and p-toluenesulfonic acid hydrate (150 mg) were added and the solution was refluxed using a Dean-Stark trap to separate water. After 4 hr, 20 ml of condensate was withdrawn and the solution was refluxed overnight. The solution was cooled to room temperature and evaporated under reduced pressure. The residue was dissolved in a solution of sodium cyanoborohydride (1.25 g) in dry methanol (75 ml) and the solution was stirred for 2 hr at room temperature. Solvent was evaporated under reduced pressure and the residue was partitioned between ethyl acetate (75 ml) and water (75 ml). The organic layer was separated and then extracted with 0.5M, pH 6.5 phosphate buffer (75 ml) and with 0.5M, pH 4.5 phosphate buffer (2×75 ml). The combined latter extracts were back-extracted with ethyl acetate (75 ml) and the combined ethyl acetate solutions were dried (Na$_2$SO$_4$) and filtered. The filtrate was evaporated to dryness and the residue was dissolved in a small volume of dichloromethane, filtered and purified by chromatography on silica gel (Waters Prep 500), eluting with a linear gradient of dichloromethane (4 L) and 5% methanol plus 0.5% conc. ammonium hydroxide in dichloromethane (4 L) followed by 3 L of the latter solvent mixture. The fraction containing the desired compound was located by tlc analysis and was evaporated to dryness to yield 113 mg of the title compound.

EXAMPLE 30

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

We claim:

1. A compound of the formula

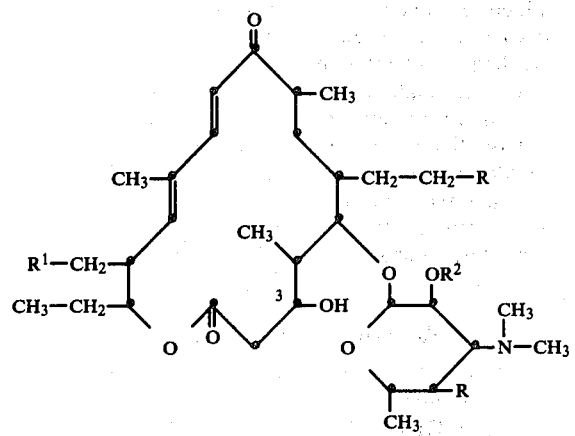

R is hydrogen, cyano, $-OR^4$, $-OAr$, $-SR^5$, azido, $-NR^6R^7$, or N-phthalimido;

$R^1$ is
  (i) hydrogen or $-OH$;
  (ii) $-OAr$, -O-tetrahydrofuranyl, -O-tetrahydropyranyl, $-SR^5$, azido, $-NR^6R^7$, or N-phthalimido;
  (iii) a monocyclic amino group of the formula $-N(CH_2)_n$ and n is an integer from 4 through 15; or a specified monocyclic amino group which is substituted at one or more of the carbon atoms by a $C_1$-$C_3$-alkyl, hydroxyl, methoxyl, ethoxyl, $-N(R^8)_2$,

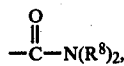

carbomethoxy, carboethoxy, or phenyl group;
  (iv) a monocyclic saturated or unsaturated nitrogen-containing heterocyclic ring bonded through the nitrogen atom, said ring having (1) from 5 to 7 ring atoms which include up to 3 additional heteroatoms selected from nitrogen, oxygen and sulfur, and (2) up to 3 substituent groups selected from methyl, ethyl and phenyl; or
  (v) a bicyclic or tricyclic secondary amino group selected from 1,2,3,4-tetrahydroquinolin-1-yl; decahydroquinolin-1-yl; 1,2,3,4-tetrahydroisoquinolin-2-yl; decahydroisoquinolin-2-yl; indolin-1-yl; isoindolin-2-yl; decahydrocyclohepta[b]pyrrol-1-yl; decahydrocyclohepta[c-]pyrrol-2-yl; decahydrocyclopent[c]azepin-2-yl; decahydrocyclopent[d]azepin-3-yl; 2,3,4,5-tetrahydro-1H-2-benzazepin-2-yl; 2,3,4,5-tetrahydro-1H-3-benzazepin-3-yl; azabicycloheptanyl; azabicyclooctanyl; azabicyclononanyl; azabicyclodecanyl or azatricyclodecanyl;

$R^2$ is hydrogen; $C_1$-$C_5$-alkanoyl; $C_1$-$C_5$-alkanoyl having from one to three halo substituents; benzoyl, phenylacetyl or phenylpropionyl; or benzoyl, phenylacetyl or phenylpropionyl having on the phenyl ring from one to five halo or methyl groups or from one to two methoxyl, nitro or hydroxyl groups;

$R^3$ is hydrogen; hydroxyl; $C_1$-$C_5$-alkanoyloxy; $C_1$-$C_5$-alkanoyloxy having from one to three halo substituents; benzoyloxy, phenylacetoxy or phenylpropionyloxy; or benzoyloxy, phenylacetoxy or phenylpropionyloxy having on the phenyl ring from one to five halo or methyl groups or from one to two methoxyl, nitro or hydroxyl groups; or

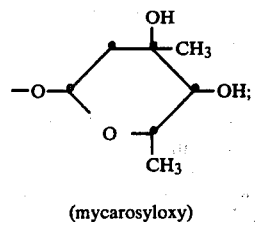

(mycarosyloxy)

$R^4$ is hydrogen; $C_1$-$C_4$-alkyl; $C_1$-$C_4$-alkyl having one or more fluoro or chloro substituents; cyclohexyl; benzyl, phenethyl or phenoxyethyl; or benzyl, phenethyl or phenoxyethyl having on the phenyl ring from one to five halo or methyl groups or from one to two methoxyl, nitro or hydroxyl groups;

Ar is
  (i) phenyl; phenyl having from one to five halo, methoxyl or $C_1$-$C_4$-alkyl substituents, or from one to two nitro, amino, methylamino, ethylamino, dimethylamino, diethylamino, $C_4$-$C_{10}$-methyleneamino, azido, hydroxy, hydroxymethyl, aminomethyl, (methylamino)methyl, (ethylamino)methyl, (dimethylamino)methyl, (diethylamino)methyl, ($C_4$-$C_{10}$-methyleneamino)methyl, formyl, acetyl, benzoyl, methoxycarbonyl, ethoxycarbonyl, carboxamido, N-methylcarboxamido, N,N-dimethylcarboxamido, cyano, phenyl, phenoxy or benzyl substitutents; or naphthyl;
  (ii) a heteroaryl group selected from pyridinyl, pyrimidinyl, pyridazinyl, pyrazinyl, triazinyl, indolyl, isoquinolinyl, quinolinyl, quinazolinyl, cinnolinyl, quinoxalinyl, phthalazinyl, benzotriazolyl, benzoxazolyl, benzimidazolyl, carbazolyl, or acridinyl; or a specified heteroaryl group having a $C_1$-$C_4$-alkyl, halo, methoxy, ethoxy, hydroxy or keto or phenyl substituent;
  (iii) $C_1$-$C_5$-alkanoyl; $C_1$-$C_5$-alkanoyl having from one to three halo substitutents; methanesulfonyl; trifluoromethanesulfonyl; benzoyl, phenylacetyl, phenylpropionyl, phenoxyacetyl, phenylsulfonyl or phenylthioacetyl; or benzoyl, phenylacetyl, phenylpropionyl, phenoxyacetyl, phenylsulfonyl or phenylthioacetyl having on the phenyl ring from one to five halo or methyl groups or from one to two methoxyl, nitro or hydroxyl groups;

$R^5$ is $C_1$-$C_4$-alkyl; $C_1$-$C_4$-alkyl having one or more fluoro or chloro substituents, cyclohexyl; phenyl, benzyl or phenethyl; phenyl, benzyl or phenethyl having on the phenyl ring from one to five halo or methyl groups or from one to two methoxyl, nitro or hydroxyl groups; a heteroaryl group selected from imidazolyl, pyrazolyl, pyridinyl, pyrimidinyl, pyrazinyl, pyridazinyl, triazinyl, triazolyl, tetrazolyl, oxazolyl, isoxazolyl, oxadiazolyl, thiazolyl, isothiazolyl, thiadiazolyl, thienyl and furanyl; or a specified heteroaryl group having a $C_1$-$C_4$-alkyl, halo, methoxy, ethoxy, hydroxy or keto or phenyl substituent;

$R^6$ is hydrogen; $C_1$-$C_6$-alkyl; $C_1$-$C_6$-alkyl having one or more fluoro or chloro substituents; phenyl; benzyl; phenethyl or $C_3$-$C_8$-cycloalkyl;

$R^7$ is an $R^6$ group or $C_1$-$C_5$-alkanoyl; $C_1$-$C_5$-alkanoyl having from one to three halo substitutents; benzoyl, phenylacetyl, phenylpropionyl, phenoxyacetyl or phenylthioacetyl; benzoyl, phenylacetyl, phenylpropionyl, phenoxyacetyl or phenylthioacetyl having on the phenyl ring from one to five halo or methyl groups or from one to two methoxyl, nitro or hydroxyl groups; or alkoxycarbonyl; and $R^8$ is hydrogen, methyl, ethyl, n-propyl or isopropyl or the $R^8$ groups taken together form a polymethylene moiety such that —$N(R^8)_2$ constitutes a cyclic amino group selected from pyrrolidinyl, piperidinyl, hexahydroazepinyl or octahydroazocinyl; provided (1) that, when R or $R^4$ is hydrogen, $R^1$ cannot be hydrogen or —OH; (2) that, when R or $R^1$ is —$NHR^6$ or $R^8$ is hydrogen, $R^2$ must be hydrogen, $R^3$ must be hydrogen, hydroxyl, or mycarosyloxy and Ar cannot be a type (iii) substituent; and (3) that, when $R^2$ is hydrogen, $R^3$ must be hydrogen, hydroxyl or mycarosyloxy; and to the acid addition salts of these compounds.

2. A compound of claim 1 wherein R is cyano.

3. A compound of claim 1 wherein R is hydrogen.
4. A compound of claim 1 wherein R is —$OR^4$.
5. A compound of claim 1 wherein R is —OAr.
6. A compound of claim 1 wherein R is —S—$R^5$.
7. A compound of claim 1 wherein R is azido.
8. A compound of claim 1 wherein R is —$NR^6R^7$.
9. A compound of claim 1 wherein R is N-phthalimido.
10. A compound of claim 1 wherein $R^1$ is hydrogen.
11. A compound of claim 1 wherein $R^1$ is —OAr.
12. A compound of claim 1 wherein $R^1$ is -O-tetrahydrofuranyl or -O-tetrahydropyranyl.
13. A compound of claim 1 wherein $R^1$ is —$SR^5$.
14. A compound of claim 1 wherein $R^1$ is azido.
15. A compound of claim 1 wherein $R^1$ is —$NR^6R^7$.
16. A compound of claim 1 wherein $R^1$ is N-phthalimido.
17. A compound of claim 1 wherein $R^1$ is a group (iii) substituent.
18. A compound of claim 17 wherein the group (iii) substituent is octahydroazocin-1-yl.
19. A compound of claim 1 wherein $R^1$ is a group (iv) substituent.
20. A compound of claim 19 wherein the group (iv) substituent is morpholino.
21. A compound of claim 1 wherein $R^1$ is a group (v) substituent.
22. A compound of claim 21 wherein the group (v) substituent is 3-azabicyclononan-3-yl.
23. A compound of claim 3 wherein $R^1$ is a group (iii), (iv) or (v) substituent.
24. A compound of claim 5 wherein $R^1$ is a group (iii), (iv) or (v) substituent.
25. A compound of claim 8 wherein $R^1$ is a group (iii), (iv) or (v) substituent.
26. A compound of claim 3 wherein $R^1$ is —OAr.
27. A compound of claim 8 wherein $R^1$ is —OAr.
28. A compound of claim 5 wherein $R^1$ is —OAr.
29. A compound of claim 1 wherein $R^3$ is hydroxyl.
30. A compound of claim 1 wherein $R^3$ is hydrogen.
31. A compound of claim 1 wherein $R^2$ is hydrogen.

* * * * *

UNITED STATES PATENT AND TRADEMARK OFFICE
CERTIFICATE OF CORRECTION

PATENT NO. : 4,468,511

DATED : August 28, 1984

INVENTOR(S) : Herbert A. Kirst and John E. Toth

It is certified that error appears in the above—identified patent and that said Letters Patent is hereby corrected as shown below:

Column 27, line 33, that part of the structural formula reading

" 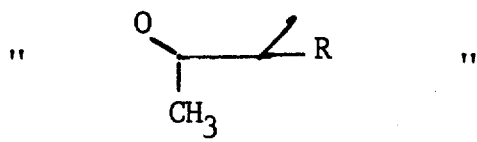 "

should read -- 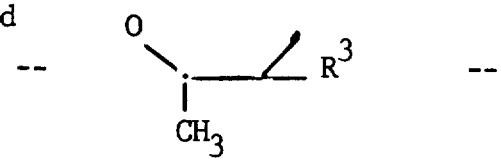 --

Column 27, line 47, "methoxy" should read -- methoxyl --.

Signed and Sealed this

Twenty-fifth Day of February 1986

[SEAL]

Attest:

DONALD J. QUIGG

Attesting Officer    Commissioner of Patents and Trademarks